United States Patent
Roberts et al.

(10) Patent No.: US 10,188,636 B2
(45) Date of Patent: Jan. 29, 2019

(54) BETAHISTINE FOR THE TREATMENT OF NEURODEGENERATIVE DISEASES

(71) Applicant: Cipla (UK) Limited, Weybridge, Surrey (GB)

(72) Inventors: Karl Roberts, Llanelli (GB); Geena Malhotra, Mumbai (IN); Kalpana Joshi, Maharashtra (IN)

(73) Assignee: Cipla Limited, Mumbai (IN)

( * ) Notice: Subject to any disclaimer, the term of this patent is extended or adjusted under 35 U.S.C. 154(b) by 0 days.

(21) Appl. No.: 15/332,189

(22) Filed: Oct. 24, 2016

(65) Prior Publication Data

US 2017/0112815 A1    Apr. 27, 2017

(30) Foreign Application Priority Data

Oct. 25, 2015   (IN) .......................... 2427/MUM/2015

(51) Int. Cl.
*A61K 31/4402*   (2006.01)
*A61K 45/06*   (2006.01)
*A61K 9/00*   (2006.01)

(52) U.S. Cl.
CPC ........ *A61K 31/4402* (2013.01); *A61K 9/0014* (2013.01); *A61K 9/0053* (2013.01); *A61K 45/06* (2013.01)

(58) Field of Classification Search
CPC .. A61K 31/4402; A61K 45/06; A61K 9/0014; A61K 9/0053
See application file for complete search history.

(56) References Cited

FOREIGN PATENT DOCUMENTS

WO    WO-2007076140 A2 *   7/2007

OTHER PUBLICATIONS

Nadafi et al (American Journal of Alzheimer's disease and other dementias, 28(4), 327-336, 2013.*
Brioni et al (The Journal of Pharmacology and Experimental Therpeutics, vol. 336 (1), pp. 38-46, 2011.*
Kubo et al.: Histamine H3 receptor antagonists for Alzheimer's disease: A systematic review and meta-analysis of randomized placebo-controlled trials [Journal of Alzheimer's Disease (2015) 48:667-671].*
Barak, "Betahistine: what's new on the agenda?", Expert Opinion on Investigational Drugs (2008) 17(5):795-804.

* cited by examiner

*Primary Examiner* — Savitha M Rao
(74) *Attorney, Agent, or Firm* — Meunier Carlin & Curfman LLC

(57) ABSTRACT

Disclosed herein are method of treating neurodegenerative diseases, including Alzheimer's disease, with the anti-histaminic drug betahistine.

5 Claims, 2 Drawing Sheets

BETAHISTINE FOR THE TREATMENT OF NEURODEGENERATIVE DISEASES

CROSS REFERENCE TO RELATED APPLICATION

This application claims the benefit of Indian Application 2427/MUM/2015, posted-dated Oct. 25, 2015.

FIELD OF INVENTION

The present invention relates to a method of treatment of neurodegenerative diseases, including Alzheimer's disease, by administering a histaminergic agent which is a histamine $H_1$-receptor agonist and histamine $H_3$-receptor antagonist to a subject in need thereof.

BACKGROUND OF THE INVENTION

Neurons build the nervous system, the system which includes the brain and spinal cord. On damage or death of these neurons, body is in no capacity to replace them and thus such conditions lead to neurodegenerative diseases which include Parkinson's, Alzheimer's and Huntington's disease.

Alzheimer's disease (AD) is a progressive neurodegenerative disease, characterized by memory loss, cognitive impairment, and functional decline. During early stages of the disease, sleep disturbances and forgetfulness are generally first presenting symptoms. In severe stages, patients with Alzheimer's disease (AD) require permanent observation, either by a home care professional or a family member.

Dementias are responsible for the greatest burden of disease with Alzheimer's. The cluster of symptoms seen in Alzheimer's disease (AD) is called dementia. Alzheimer's disease (AD) comprises approximately 60-80% of the total population suffering from dementia. The risk of developing Alzheimer's disease (AD) is believed to be determined by a combination of genetic, metabolic, behavioral, and environmental factors.

A progressive dementia associated with Alzheimer's disease is characterized by pronounced neurodegeneration in the entorhinal cortex, hippocampal CA1 and subiculum. The neurodegeneration present in hippocampus, cortex, and entorhinal cortex in Alzheimer's disease (AD) are the products of several neurodegenerative processes that occur at different stages of disease. Cholinergic abnormalities are the most problematic neurotransmitter deficiencies in Alzheimer's disease (AD). Acetylcholine (Ach) acts on muscarinic and nicotinic receptors in both peripheral and central nervous systems. Increased activation of nicotinic receptors in hippocampus and cortex elicits a therapeutic response, improving cognition and memory. Many current Alzheimer's disease (AD) therapies focus on the inhibition of Acetylcholine esterase (AChE), the enzyme that hydrolyzes Acetylcholine (Ach). These therapies may provide symptomatic relief in Alzheimer's disease (AD).

Alzheimer's disease is the leading cause of dementia worldwide. An estimated 5.2 million Americans of all ages have Alzheimer's disease in 2014. This includes an estimated 5 million people age 65 and older and approximately 200,000 individuals under age 65 who have younger-onset Alzheimer's. In US, one in nine people age 65 and older (11 percent) has Alzheimer's disease, about one-third of people age 85 and older (32 percent) have Alzheimer's disease. Of those with Alzheimer's disease, the vast majority (82 percent) are age 75 or older.

Acetylcholineesterase inhibitors (more often called as Cholinesterase inhibitors) and NMDA receptor antagonists are the two type of medications used in Alzheimer's treatment. The most common treatment for Alzheimer's disease (AD) is Cholinesterase inhibitors such as donepezil, rivastigmine, and galantamine. Cholinesterase inhibitors curb the breakdown of acetylcholine, the neurotransmitter in the brain, which is responsible for memory and learning. Cholinesterase inhibitors increase the levels of acetylcholine in the brain and may slow down the progression of symptoms. Memantine is a NMDA receptor antagonist which is generally recommended for the treatment of moderate to severe Alzheimer's disease.

The currently available therapies for Alzheimer's disease (AD) provide only symptomatic relief, and may not cure or prevent the disease from worsening over time. Secondly, a particular drug may not be beneficial to a patient considering the side effects suffered by a particular individual considering the stage of the disease. Since Alzheimer's disease (AD) is multifarious, with various etiologies, it seems unlikely that any one treatment or approach may be able to cure it. The modern approaches for treatment and research are focusing on several different aspects, like, maintaining mental function, managing behavioral symptoms, slowing or delaying the symptoms of the disease, preserving cognitive and functional processes, improving the patient's quality of life, delaying institutionalization, decreasing the caregiver burden.

Though the thought process in the same context is ongoing one may still look into approaches which can give promising results in this direction. Approaches considering the activity and mechanisms of the existing array of drugs or actives in order to treat Alzheimer's disease may be a techno-economical path forward in the desired direction.

SUMMARY OF THE INVENTION

Figure 1:
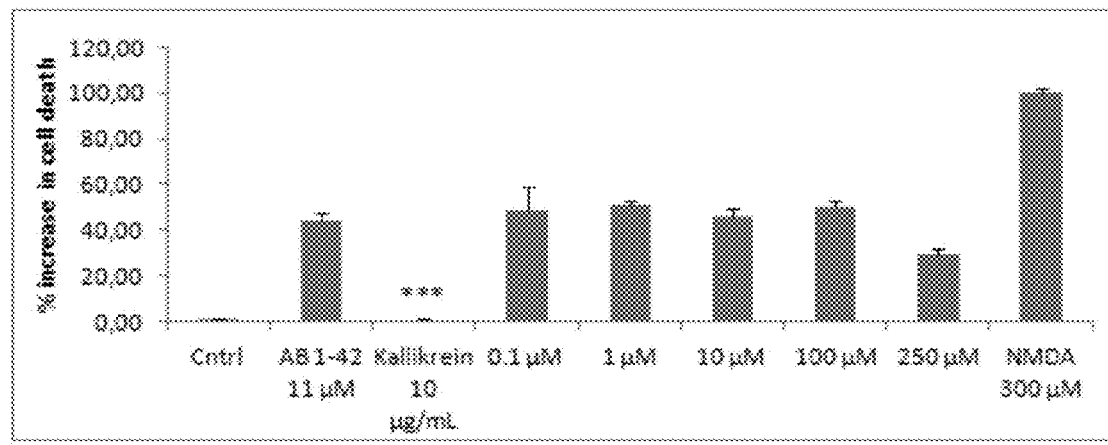
FIG. 1 includes a depiction of the effect of Betahistine of Aβ 1-42-induced percent increase in in primary rat mixed cortical cultures.

According to an aspect of the present invention, there is provided a method of treating a neurodegenerative disease, for instance, Alzheimer's disease, comprising administrating a histaminergic agent to a patient in need thereof.

According to another aspect of the present invention, there is provided a method of treating a neurodegenerative disease, for instance, Alzheimer's disease, comprising administrating a histaminergic agent which is a H1-receptor agonist and histamine H3-receptor antagonist.

According to yet another aspect of the invention, there is provided the use of a histaminergic agent which is a histamine H1-receptor agonist and histamine H3-receptor antagonist for the treatment of a neurodegenerative disease, for instance, Alzheimer's disease.

According to further aspect of the invention there is provided a pharmaceutical composition comprising a histaminergic agent which is a histamine $H_1$-receptor agonist and histamine H₃-receptor antagonist, effective for treating neurodegenerative diseases, for instance, Alzheimer's disease.

DESCRIPTION OF THE INVENTION

Before the present methods and systems are disclosed and described, it is to be understood that the methods and systems are not limited to specific methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes¬from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

Betahistine is a histaminergic agent, used in the treatment of Ménière's disease. Betahistine acts as a histamine H₁-receptor agonist and histamine H₃-receptor antagonist. Betahistine may be chemically represented as—

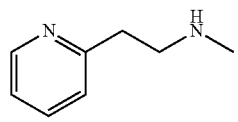

Betahistine is commonly prescribed to patients with balance disorders or to alleviate vertigo symptoms associated with Ménière's disease. Ménière's disease is a disease where an accumulation of fluid in the inner ear causes a build-up of pressure. Patients with Ménière's disease have vertigo (a spinning sensation), often associated with feeling sick or vomiting, tinnitus (ringing in the ear) and hearing loss.

Betahistine was first registered in Europe in 1970 as an anti-vertigo drug for the treatment of Ménière's disease (Brand names; Veserc, Serc, Hiserk, Betaserc). It is available as 8 & 16 mg tablets for oral use.

Betahistine, is an analogue of histamine, a naturally-occurring substance in the body that is involved in many processes. In Ménière's disease, betahistine is thought to attach to some receptors to which histamine normally attaches. This dilates the blood vessels in the inner ear, thus helping the pressure to drop and relieving the symptoms of the disease.

Betahistine has a very strong affinity as an antagonist for histamine H₃ receptors and a weak affinity as an agonist for histamine H₁ receptors. Betahistine has two modes of action. Primarily, it has a direct stimulating (agonistic) effect on H1 receptors located on blood vessels in the inner ear. This gives rise to local vasodilation and increased permeability, which helps to reverse the underlying problem of endolymphatic hydrops. More importantly, betahistine has a powerful antagonistic effects at H₃ receptors, thereby increasing the levels of neurotransmitters histamine, acetylcholine, norepinephrine, and serotonin released from the nerve endings. The increased amounts of histamine released from histaminergic nerve endings can stimulate receptors. This stimulation explains the potent vasodilatory effects of betahistine in the inner ear that are well documented. It is postulated that betahistine increases the levels of serotonin in the brainstem which inhibits the activity of vestibular nuclei. Means, betahistine reduce the firing rate of vestibular nuclei in the brain.

Further, H₃-receptor antagonist is a classification of drugs used to block the action of histamine at the H₃ receptor. Unlike the H₁ and H₂ receptors which have primarily peripheral actions, but cause sedation if they are blocked in the brain, H₃ receptors are primarily found in the brain and are inhibitory autoreceptors located on histaminergic nerve terminals, which modulate the release of histamine. Histamine release in the brain triggers secondary release of excitatory neurotransmitters such as glutamate and acetylcholine via stimulation of H₁ receptors in the cerebral cortex. Consequently unlike the H₁ antagonist antihistamines which are sedating, H₃ antagonists have stimulant and nootropic effects.

The inventors of the present invention have found that the H₃-receptor antagonist activity of betahistine exhibits a significant role in treatment of Alzheimer's disease.

The term betahistine is used in broad sense to include not only "betahistine" per se but also its pharmaceutically acceptable derivatives thereof. Suitable pharmaceutically acceptable derivatives include pharmaceutically acceptable salts, solvents, hydrates, anhydrates, polymorphs and the like.

Pharmaceutically acceptable salts are salts that retain the desired biological activity of the parent compound and do not impart undesirable toxicological effects. Examples of such salts are acid addition salts formed with inorganic acids, for example, hydrochloric, hydrobromic, sulfuric, phosphoric, and nitric acids and the like; salts formed with organic acids such as acetic, oxalic, tartaric, succinic, maleic, fumaric, gluconic, citric, malic, methanesulfonic, p-toluenesulfonic, napthalenesulfonic, and polygalacturonic acids, and the like; salts formed from elemental anions such as chloride, bromide, and iodide; salts formed from metal hydroxides, for example, sodium hydroxide, potassium hydroxide, calcium hydroxide, lithium hydroxide, and magnesium hydroxide; salts formed from metal carbonates, for example, sodium carbonate, potassium carbonate, calcium carbonate, and magnesium carbonate; salts formed from metal bicarbonates, for example, sodium bicarbonate and potassium bicarbonate; salts formed from metal sulfates, for example, sodium sulfate and potassium sulfate; and salts formed from metal nitrates, for example, sodium nitrate and potassium nitrate. Pharmaceutically acceptable and non-pharmaceutically acceptable salts may be prepared using procedures well known in the art, for example, by reacting a sufficiently basic compound such as an amine with a suitable acid comprising a physiologically acceptable anion. Alkali metal (for example, sodium, potassium, or lithium) or alkaline earth metal (for example, calcium) salts of carboxylic acids can also be made.

Since betahistine contains two basic nitrogen atoms, betahistine can exist either as a monocation or di-cation. Exemplary di-cations include betahistine dihydrochloride. In some embodiments, betahistine is administered as a monocation, while in other embodiments, betahistine is administered as a dication.

Betahistine can be used to treat one or more neurodegenerative diseases, e.g., diseases characterized by a progressive loss of neuron function or structure. Exemplary neurodegenerative diseases include Alzheimer's disease, Parkinson's disease, Huntington's disease, amyotrophic lateral sclerosis, corticobasal degeneration, Battten disease and others. In a preferred embodiment, the neurodegenerative disease is Alzheimer's disease. Administration of betahistine can slow neurodegeneration (i.e., the rate at which neurons die or become nonfunctional).

Betahistine can be used to treat neurodegenerative diseases in a human patient. In some instances, betahistine can be used to neurodegenerative disease, for instance, Alzheimer's disease, in a younger patient, for instance, a patient less than 65 years, less than 60 years old, less than 55 years old, less than 50 years or, or even less than 45 years old.

In some instances, betahistine can be used to alleviate, reduce, or eliminate one or more symptoms associated with neurodegeneration. By way of example, administration of betahistine can alleviate short-term memory loss, paraphasias, rigidity, akinesia, aggression, sundowning, disequilibrium, dystonia, apraxia, myoclonus, dysphagia, agnosia, visual and/or coginitive impairment and the like.

In some embodiments, betahistine is administered as part of a pharmaceutical composition. Suitable pharmaceutical compositions include, but are not limited to, unit dosage forms including tablets, capsules (filled with powders, pellets, beads, mini-tablets, pills, micropellets, small tablet units, multiple unit pellet systems (MUPS), disintegrating tablets, dispersible tablets, granules, and microspheres, multiparticulates), sachets (filled with powders, pellets, beads, mini-tablets, pills, micropellets, small tablet units, MUPS, disintegrating tablets, dispersible tablets, granules, and microspheres, multiparticulates), powders for reconstitution and sprinkles. Other dosage forms include controlled release formulations, lyophilized formulations, modified release formulations, delayed release formulations, extended release formulations, pulsatile release formulations, dual release formulations and the like. Liquid and semisolid dosage form (liquids, suspensions, solutions, dispersions, ointments, creams, emulsions, microemulsions, sprays, spot-on), injection preparations, parenteral, topical, patches, inhalations, buccal, nasal etc. may be used to administer betahistine.

The inventors of the present invention have also found that the solubility properties of betahistine are improved by nano-sizing thus leading to better bioavailability and dose reduction of the drug. In some embodiments, betahistine may be present in the form of nanoparticles which have an average particle size of less than 2,000 nm, less than 1,500 nm, less than 1,250 nm, less than 1,000 nm, less than 750 nm, or less than 500 nm.

Suitable excipients may be used for formulating the dosage forms according to the present invention such as, but not limited to, surface stabilizers or surfactants, viscosity modifying agents, polymers including extended release polymers, stabilizers, disintegrants or super disintegrants, diluents, plasticizers, binders, glidants, lubricants, sweeteners, flavoring agents, anti-caking agents, opacifiers, antimicrobial agents, antifoaming agents, emulsifiers, buffering agents, coloring agents, carriers, fillers, antiadherents, solvents, taste-masking agents, preservatives, antioxidants, texture enhancers, channeling agents, coating agents or combinations thereof.

Betahistine can be administered according to various dosing regimens. For instance, betahistine can be administered once a day, twice a day, three times per day, or even more than three times a day. In some instance, betahistine can be administered less than once daily, for instance, once every two days, once every three days, once every five days, once every seven days, once every ten days, once every fourteen days, once every twenty-eight days or once every month. The betahistine can be administered such that the total weekly dose is at least 50 mg, at least 100 mg, at least 250 mg, at least 500 mg, at least 750 mg, at least 1,000 mg, at least 1,250 mg, at least 1,500 mg, at least 1,750 mg, or at least 2,000 mg. In some instances, the total weekly dose can be from 5-5,000 mg, 10-5,000 mg, 10-2,500 mg, 50-2,500 mg, 100-2,500 mg, 100-2,000 mg, 250-2,000 mg or 500-2,000 mg.

In some embodiments, it is preferred to administer betahistine using a transdermal composition, such as a patch, ointment, lotion, gel, spray and the like. Ointments, lotions, gels, sprays and the like may be administered according to dosing regimens previously mentioned. For instance, transdermal compositions can be applied once, twice, three-times or more a day, or can be applied every other day, once every three days, every five days, every seven days, every fourteen days, every twenty-eight days, or once a month. Patch formulations may be continuously worn, wherein a patch is replaced by a new patch once a day, every two days, every three days, every four days, every five days, every six days, every seven days, or more. In other cases, a patch may be worn intermittently, for instance, once, twice or three times day for a period of no more than 30, 60, 120, 180, 240, 300, 360, 420, 480, 540 or 600 minutes. In some cases, a patch can be worn once every other day, every third day, every fourth day, every fifth day, every sixth day, or every seventh day for a period of no more than 30, 60, 120, 180, 240, 300, 360, 420, 480, 540 or 600 minutes.

Exemplary transdermal formulations can contain betahistine blended with a carrier and other excipients, e.g., antioxidants (tocopherols, BHT, ascorbic acid and esters thereof, BHA, gallate salts such as propyl gallate, and the like), penetration enhancers (azone, pyrrolidones, fatty acids, essential oils, terpenes, terpenoids, oxazolidinones, ureas, and the like), plasticizers (polyoxyethylene fatty ($C_{12}$-$C_{18}$) alcohol ethers, polyoxyethylene fatty ($C_{12}$-$C_{18}$) alcohol esters, fatty acids ($C_{12}$-$C_{18}$), fatty esters ($C_{12}$-$C_{18}$), triacetin, glycerin derivatives, adipic acid derivatives and the like). Suitable carriers include hydrophilic polymers like poly(meth)acrylates, e.g., poly(meth)acrylate derived from $C_1$-$C_4$ esters of (meth)acrylic acid, including copolymers, poly(meth)acrylates having mixtures of cationic and neutral ester groups—such polymers are available under the EUDRAGIT® brand (Rohm); for instance EUDRAGIT RS 100® or EUDRAGIT E 100®.

The betahistine can be present in the transdermal composition in an amount from 1-50% by weight of the composition, 5-50% by weight of the composition, 5-40% by weight of the composition, 10-40% by weight of the composition, 15-40% by weight of the composition, 20-40% by weight of the composition, or 25-35% by weight of the composition. Typically the antioxidant is present in an amount from 0.1-1% by weight of the composition. When a plasticizer is present, the weight ratio of carrier polymer to plasticizer is from 20:1 to 1:5, 10:1 to 1:1, or 10:1 to 5:1. When a penetration enhancer is present, the weight ratio of carrier polymer to penetration enhancer is from 20:1 to 1:1, from 10:1 to 2:1, or from 10:1 to 5:1.

When betahistine is administered as a transdermal formulation, betahistine can be administered at a rate of 1-500 mg/24 hr, 1-250 mg/24 hr, or 1-100 mg/24 hr.

In some embodiments, the transdermal formulation is applied as a patch. The formulation may include a backing layer, having a thickness from about 2-50 μm, from about 2-25 μm, from about 2-20 μm, or from about 5-20 μm. The backing layer may be a single layer, for instance of PET foil, or may be a laminate of multiple layers. The transdermal formulation may be present on the backing layer at a thickness from 10-300 μm, from 10-200 μm, from 10-150 μm, from 20-150 μm, from 30-125 μm, or from 50-125 μm. The transdermal formulation may be covered with a releaseable liner that protects the formulation until it is applied to the skin of a patient.

In some embodiments, betahistine may be administered along with one or more other agents for the treatment of neurodegenerative disease. The agent can be an acetylcholinesterase inhibitor or NMDA receptor antagonist. Suitable agents include memantine, galantamine, rivastigmine, or donepezil. In some instances, betahistine can be administered along with an antidepressant, for instance an selective serotonin reuptake inhibitor, a serotonin-norepinephrine reuptake inhibitor, a tricyclic antidepressant, a monoamine oxidase inhibitor, a tetracyclic antidepressant, or In certain embodiments, the betahistine and other agent(s) can be provided in a unitary dosage form, e.g., when betahistine and other agent(s) are both present in the same dosage form. In other embodiments, betahistine and the other agent(s) can be administered as separate dosage forms, either at the same or different time. As used herein, "at the same time" refers to near simultaneous administration, i.e., both agents are administered within 30, 25, 20, 15, 10, 5 or 2 minutes of each other. When betahistine is administered at different times that the other agent, the administration of the agents can be separated by a period of at least 4, 6, 8, 12 or 24 hours. For instance, one agent may be administered in the morning and the other administered in the evening. When both betahistine and the other agent(s) are formulated for transdermal delivery, both betahistine and other agent may be applied to the skin at the same time, or at separate times. In the case of patch formulations, separate patches may be applied to the skin at the same time. In other cases, after a betahistine patch is removed, a patch containing another agent may be applied, and the cycle may be repeated as needed. In some cases, after one patch is removed, the other patch is immediately applied, while in others, there is a period of at least 1, 2, 3, 4, 5, 6, or 7 days in which no patch is worn.

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric.

Example 1: Cell Culture and In Vitro Cytotoxicity Assay

Mixed cortical cultures are prepared from E18 Wistar rat embryos. The cortices are dissected out and tissue cut into small pieces. The cells are separated by 15-min incubation with DNase and papain. The cells are collected by centrifugation (1500 rpm, 5 min). The tissue is triturated with a pipette and the cells are plated on poly-L-lysine—coated 96-well plates, 120,000 cells/well, in MEM (2 g/L glucose) supplemented with 2 mM glutamine, 10 μg/mL gentamicin, 10% heat-inactivated fetal bovine serum (FBS-HI) and 10% heat-inactivated horse serum (HS-HI). After 3-4 h, the medium is changed to MEM (2 g/L glucose) supplemented with 2 mM glutamine, 10 μg/mL gentamicin, 5% HS-HI. After three days in vitro, medium containing MEM (Minimum Essential Media) (2 g/L glucose) supplemented with glutamine, gentamicin and 5% both serum is changed to the cells. On day 6 in vitro, the unwanted cell division is inhibited by adding cytosine arabinoside (10 μM final concentration) for 24 h. The cultures refed with MEM (2 g/L glucose) supplemented with glutamine, gentamicin and 5% HS-HI before experiments.

Aß1-42 Exposure

The wells in good shape are chosen for experiment on day 10 in vitro. Test compounds are diluted in MEM (2 g/L glucose) supplemented with L-glutamine, gentamicin, and 5% HS-HI. As a control for total neuronal death, 300 μM NMDA (N-Methyl-D-aspartic acid) for 72 hours is used, and Aß1-42 for 72 hours is used to induce approximately 30-60% cell death. Kallikrein (10 μg/mL) serve as positive control for inhibition of Aß1-42-induced cell death. Wells treated with medium only serve as 0-control. Test compounds are pipetted to the cells 30 minutes before adding Aß1-42 for 72 hours.

Assessment of Cell Death (LDH [Lactate dehydrogenase] Measurement) After 72 hours the culture media of all wells are collected and possible cell debris is removed by centrifugation (13 000 rpm, 3 minutes). A-100-μl aliquot is pipetted into a micro titer plate, and equal amount of LDH reagent is pipetted to the wells. The absorbance at 340 nm is measured immediately using a 3-min kinetic measurement protocol in Multiskan FC ELISA reader (Thermo, Finland). The change in absorbance/min is determined, which is directly proportional to the released LDH (=cell death).

As shown in FIG. 1, betahistine showed profound protective effect against Aβ 1-42-induced cell death in primary rat mixed cortical cultures when tested at 37° C., 5% $CO_2$ for 72 hours at varied concentrations.

Example 2: In Vivo Efficacy Study

I. Effect of Betahistine on Cognition and Beta Amyloid Load in APPSwDI/NOS2−/− Transgenic Mice The purpose of this study was to investigate the effects of Betahistine treatment in the Alzheimer's disease (AD) transgenic mouse model APPSwDI/NOS2−/−. APPSwDI/NOS2−/− are double transgenic mice which display impared spatial memory, neuronal loss and neurofibrillary tangle like pathology.

At the age of ~12.5 months the mice were subjected to once-a-day p.o. vehicle or betahistine. Treatment was continued for 2.5 months. After two months of treatment, starting at the age of ~14.5 months the mice were subjected to Contextual Fear Conditioning (CFC) test. The test was performed as follows Day 1

Training consisted of placing a mouse in a chamber, bright house light on, and allowing exploration for 2 min. Afterward an auditory cue (1700 Hz, 80 dB, conditioned stimulus (CS)) was presented for 15 s. A 2 s foot shock (1.5 mA; unconditioned stimulus (US)) was administered for the final 2 s of the CS. This procedure was repeated, and the mouse was removed from the chamber 30 s later.

Day 2

Twenty hours (±30 min) after the training, the mouse was returned to the same chamber in which the training occurred (memory for context), and freezing behavior was recorded by a computerized camera tracking system. The automated Freeze Frame system, which digitized the video signal at 4 Hz and compared movement of the mouse frame by frame, was used to score the amount of freezing. At the end of the 5 min context test, the mouse was returned to its home cage. Freezing scores for each subject were expressed as a percentage for memory for context.

Figure 2:
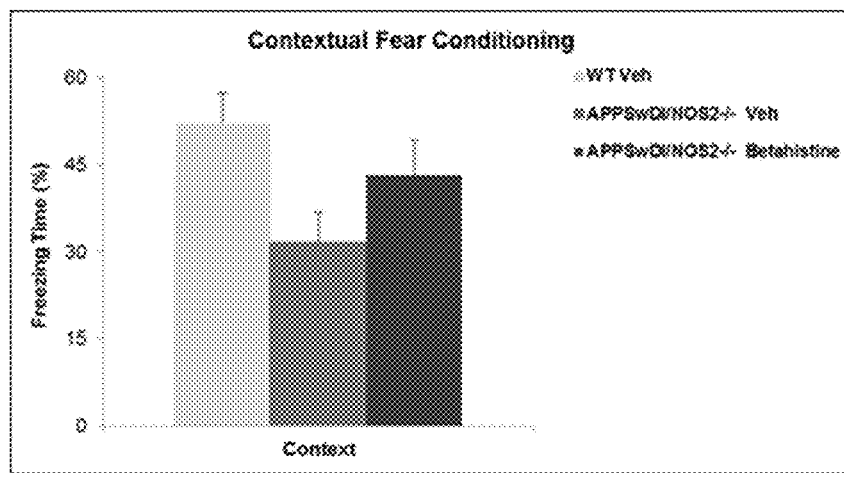
FIG. 2 includes a depiction of the Freezing score in APPSwDI/NOS2−/− Mice on treated with Betahistine in contextual fear conditioning test.

Results:

As shown in FIG. 2, APPSwDI/NOS2−/− vehicle treated mice has lower freezing scores compared to WT vehicle treated mice (p<0.05). In addition, APPSwDI/NOS2−/− had improved freezing score when treated with betahistine.

II. Efficacy Study of Betahistine in the Intra-Cerebroventricular Streptozotocin-Induced Alzheimer's Disease Model Seven-week-old male C57BL/6 mice were obtained from Japan SLC, (Japan). The animals were maintained in a SPF facility under controlled conditions of temperature (23±2° C.), humidity (45±10%), lighting (12-hour artificial light and dark cycles; light from 8:00 to 20:00) and air exchange. On day 0 and day 2, 60 mice were anesthetized with pentobarbital sodium (Kyoritsu Seiyalu, Japan) and intracerebroventricularly (icv) administered two doses of streptozotocin (STZ, Sigma-Aldrich, USA) in saline at a dose of 3 mg/kg. The icv-STZ-induced Alzheimer's disease model mice were divided into 6 groups of 10 mice based on their body weight on the day before the start of the treatment. Betahistine was orally administered at doses of 30 and 100 mg/kg once daily from day 0 do day 14. Donepezil was orally administered at a dose of 0.5 mg/kg once daily from day 0 to day 14.

Histological Analysis

Figure 3:
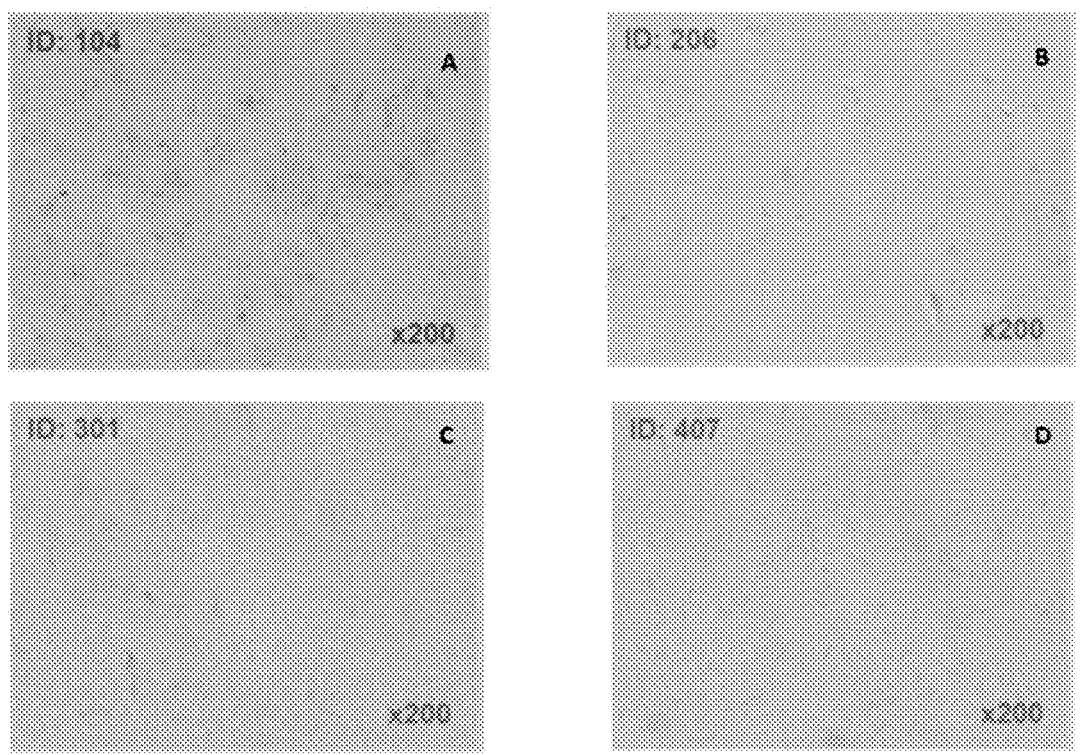
FIG. 3 includes a depiction of the quantitative analysis of GFAP positive areas (A) STZ+Vehicle, (B) STZ+Betahistine 30 mg/kg, (C) STZ+Betahistine 100 mg/kg, (D) STZ+Donepezil

To investigate neuro-inflammation, the levels of GFAP, a marker of astrocytes, were measured. For immunohistochemistry, sections were cut from frozen brain tissues embedded in Tissue-Tek O.C.T. compound and fixed in acetone. Endogenous peroxidase activity was blocked using 0.03% $H_2O_2$ for 5 minutes, followed by incubation with Block Ace (Dainippon Sumitomo Pharma Co. Ltd., Japan) for 10 minutes. The sections were incubated with a 500-fold dilution of anti-GFAP antibody (Abcom) at room temperature for 1 hour. The sections were then incubated with biotin-conjugated secondary antibody (VECTASTAIN Elite ABC kit, Vector laboratories) followed by ABC reagent each for 30 minutes at room temperature. Enzyme-substrate reactions were performed using 3,3'-diaminobenzidine/$H_2O_2$ solution (Nichirei Bioscience Inc.). For quantitative analysis of GFAP-positive areas, bright field images of GFAP-immunostained sections were captured using a digital camera (DFC295; Leica, Germany) at 200-fold magnification, and the positive areas in 3 fields/section were measured using ImageJ software. Betahistine treatment groups, and the donepezil group showed significant decreases in GFAP-positive area compared with the Vehicle group (FIG. 3).

PCR to Check Expression Levels of MAP2 Genes

Expression levels of MAP2, a cytoskeletal modulator that has been implicated in the pathogenesis of Alzheimer's disease and a member of MAP2/tau family, was measured by quantitative RT-PCR. Total RNA was extracted from brain samples using RNAiso (Takara Bio, Japan) according to the manufacturer's instructions. One μg of RNA was reverse-transcribed using a reaction mixture containing 4.4 mM MgCl2 (F. Hoffmann-La Roche, Switzerland), 40 U RNase inhibitor (Toyobo, Japan), 0.5 mM dNTP (Promega, USA), 6.28 μM random hexamer (Promega), 5× first strand buffer (Promega), 10 mM dithiothreitol (Invitrogen, USA) and 200 U MMLV-RT (Invitrogen) in a final volume of 20 μL. The reaction was carried out for 1 hour at 37° C., followed by 5 minutes at 99° C. Real-time PCR was performed using real-time PCR DICE and SYBR premix Taq (Takara Bio). To calculate the relative mRNA expression level, the expression of each gene was normalized to that of reference gene GAPDH. Both betahistine and donepezil showed significant down regulation of MAP2 mRNA expression (Table 1).

Gene Expression Analysis

TABLE 1

Expression levels of MAP2 gene

| Parameter (Mean ± SD) | Vehicle (n = 10) | Betahistine low dose (n = 10) | Betahistine high dose (n = 10) | Donepezil (n = 10) |
|---|---|---|---|---|
| MAP2 | 1.0 ± 0.4 | 0.7 ± 0.2 | 0.7 ± 0.2 | 0.7 ± 0.2 |

Example 3: Betahistine Formulations

| Ingredients | Qty/tab (mg) |
|---|---|
| Betahistine Dihydrochloride | 8-24 |
| Mannitol | 30-120 |
| Microcrystalline cellulose | 60-200 |
| Povidone | 4-15 |
| Crospovidone | 5-15 |
| Colloidal anhydrous silica | 1-10 |
| Hydrogenated Castor Oil/ magnesium stearate | 1-5 |
| Purified Water | q.s. |

Process:
1. Mannitol, microcrystalline cellulose, crospovidone, colloidal anhydrous silica, hydrogenated castor oil/ magnesium stearate were sifted through specified mesh.

2. Microcrystalline cellulose and mannitol were dry mixed in a suitable mixer.
3. Betahistine Dihydrochloride was dissolved in specified quantity of purified water under stirring to obtain the drug solution.
4. Povidone was added to the drug solution obtained in step (3) under stirring to get a clear drug binder solution.
5. The dry mix obtained in step (2) was granulated with the drug binder solution obtained in step (4) to obtain the granules.
6. The granules obtained in step (5) were, dried, sized and were blended with Crospovidone & Colloidal anhydrous silica.
7. The granules obtained in step (6) were lubricated with Hydrogenated castor oil/magnesium stearate.
8. The lubricated granules obtained in step (7) were compressed into tablets.

| Ingredients | Qty/tab (mg) |
| --- | --- |
| Betahistine | 8-24 |
| Lactose monohydrate | 40-120 |
| Microcrystalline Cellulose | 75-225 |
| Hypromellose | 60-180 |
| Povidone | 10-30 |
| Water | q.s. |
| Hypromellose (K4M/K100M) | 50-150 |
| Colloidal anhydrous silica | 2-6 |
| Microcrystalline Cellulose | 10-30 |
| Magnesium stearate | 1-5 |

Process:
1. Betahistine, lactose, povidone, microcrystalline cellulose and hypromellose were loaded in suitable equipment and dry mixed
2. The dry mix obtained in step (1) was granulated with water.
3. The granules obtained in step (2) were dried and sized and blended with hypromellose, silicon dioxide and microcrystalline cellulose.
4. The blended granules of step (3) were lubricated with magnesium stearate.

The lubricated granules were compressed into tablets.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A method of treating a neurodegenerative disease, comprising administering to a subject in need thereof, a therapeutically effective amount of betahistine or a pharmaceutically acceptable salt thereof, wherein the neurodegenerative disease is Alzheimer's disease and wherein the betahistine or a pharmaceutically acceptable salt thereof is administered orally in an amount from 250-5,000 mg/week with a pharmaceutically acceptable carrier or excipients.

2. The method of claim 1, wherein the betahistine or a pharmaceutically acceptable salt thereof is administered daily.

3. The method of claim 1, wherein betahistine or a pharmaceutically acceptable salt thereof is administered at least once daily.

4. The method of claim 1, wherein the betahistine or pharmaceutically acceptable salt thereof is administered in combination with one or more other therapeutics.

5. The method of claim 4, wherein the other therapeutic comprises an acetylcholinesterase inhibitor or an NMDA receptor antagonist.

* * * * *